United States Patent
Govari

(12) 
(10) Patent No.: US 6,201,387 B1
(45) Date of Patent: Mar. 13, 2001

(54) MINIATURIZED POSITION SENSOR HAVING PHOTOLITHOGRAPHIC COILS FOR TRACKING A MEDICAL PROBE

(75) Inventor: Assaf Govari, Kiryat Haim (IL)

(73) Assignee: Biosense, Inc., New Brunswick, NJ (US)

( * ) Notice: Subject to any disclaimer, the term of this patent is extended or adjusted under 35 U.S.C. 154(b) by 0 days.

(21) Appl. No.: 09/160,063

(22) Filed: Sep. 24, 1998

Related U.S. Application Data
(60) Provisional application No. 60/061,269, filed on Oct. 7, 1997.

(51) Int. Cl.[7] ........................................................ A61B 5/06
(52) U.S. Cl. ...................... 324/207.17; 600/424; 128/899
(58) Field of Search .................. 324/207.17, 207.22, 324/207.26, 207.23; 336/200, 232; 128/899; 600/409, 424

(56) References Cited

U.S. PATENT DOCUMENTS

| | | | |
|---|---|---|---|
| 3,868,565 | 2/1975 | Kuipers | 324/34 R |
| 4,054,881 | 10/1977 | Raab | 343/112 R |
| 4,560,930 | 12/1985 | Kouno | 324/207 |
| 4,613,866 | 9/1986 | Blood | 343/448 |
| 4,642,786 | 2/1987 | Hansen | 364/559 |
| 4,651,536 | 3/1987 | Gaal | 33/533 |
| 5,042,486 | 8/1991 | Pfeiler et al. | 128/653 R |
| 5,211,165 | 5/1993 | Dumoulin et al. | 128/653.1 |
| 5,253,647 | 10/1993 | Takahashi et al. | 128/653.1 |
| 5,273,025 | 12/1993 | Sakiyama et al. | 128/6 |
| 5,295,486 | 3/1994 | Wollschlager et al. | 128/661.01 |
| 5,391,199 | 2/1995 | Ben-Haim | 607/122 |
| 5,425,367 | 6/1995 | Shapiro et al. | 128/653.1 |
| 5,429,132 | 7/1995 | Guy et al. | 128/653.1 |
| 5,443,489 | 8/1995 | Ben-Haim | 607/115 |
| 5,558,091 | 9/1996 | Acker et al. | 128/653.1 |
| 5,729,129 | 3/1998 | Acker | 324/207.12 |
| 5,786,690 | * | 7/1998 | Kirtley et al. | 324/247 |

FOREIGN PATENT DOCUMENTS

| | | | |
|---|---|---|---|
| WO 94/00050 | 1/1994 | (WO) | A61B/5/02 |
| WO 94/04938 | 3/1994 | (WO) | G01S/3/14 |
| WO 96/05768 | 2/1996 | (WO) | A61B/5/06 |

* cited by examiner

*Primary Examiner*—Walter Snow
(74) *Attorney, Agent, or Firm*—Louis J. Capezzuto

(57) ABSTRACT

A miniature coil assembly for transmitting or receiving magnetic waves comprises a plurality of coils wherein each coil has a respective axis. The coil assembly is assembled such that at least two of the axes are mutually linearly independent, and such that all of the plurality of coils are contained within a volume having a cross-sectional area less than 1.0 mm$^2$. At least two of the coils are photolithographic coils.

17 Claims, 4 Drawing Sheets

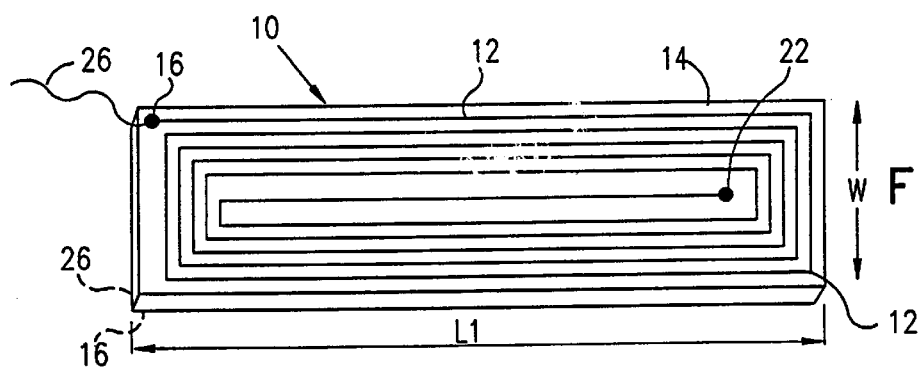
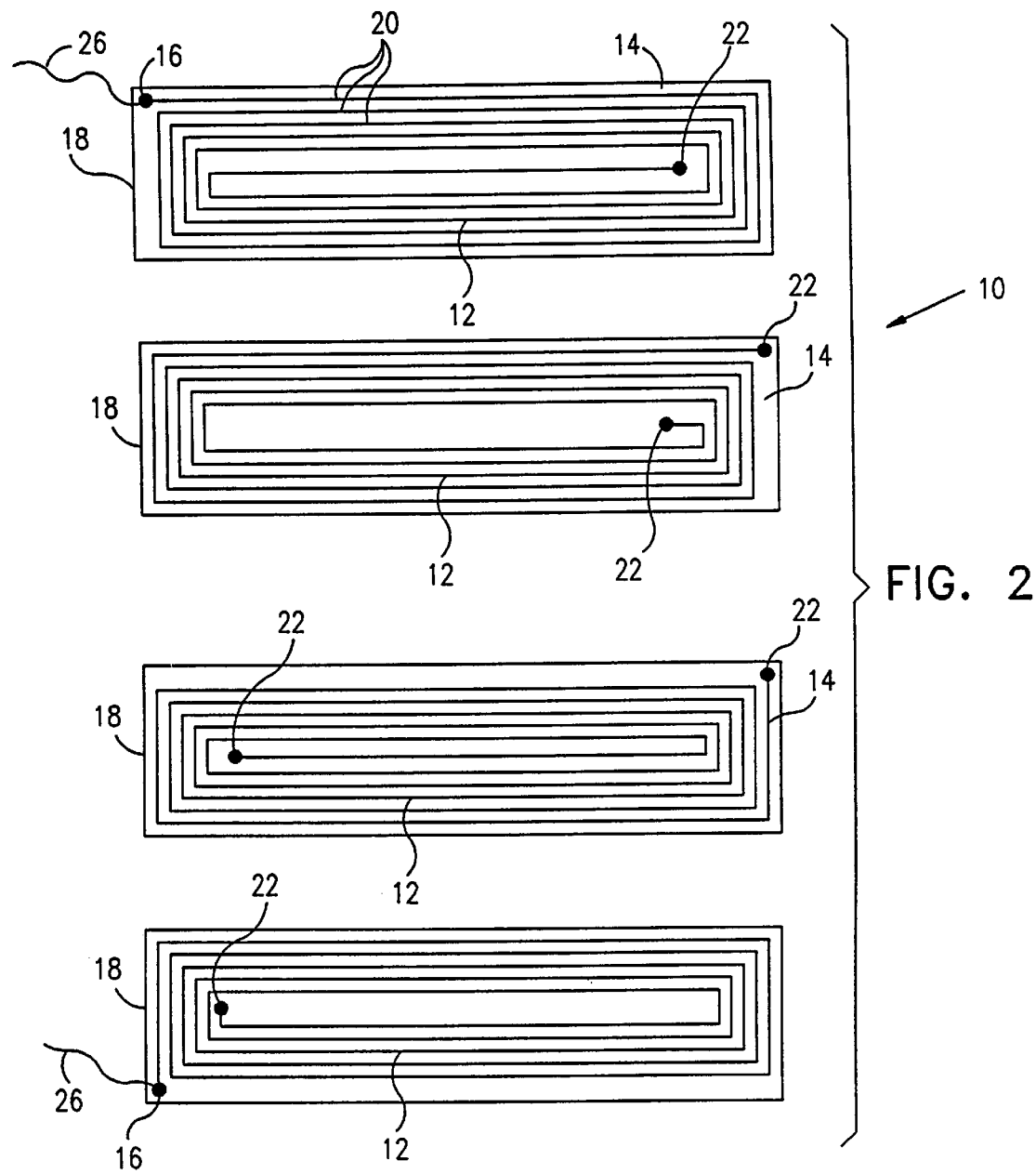

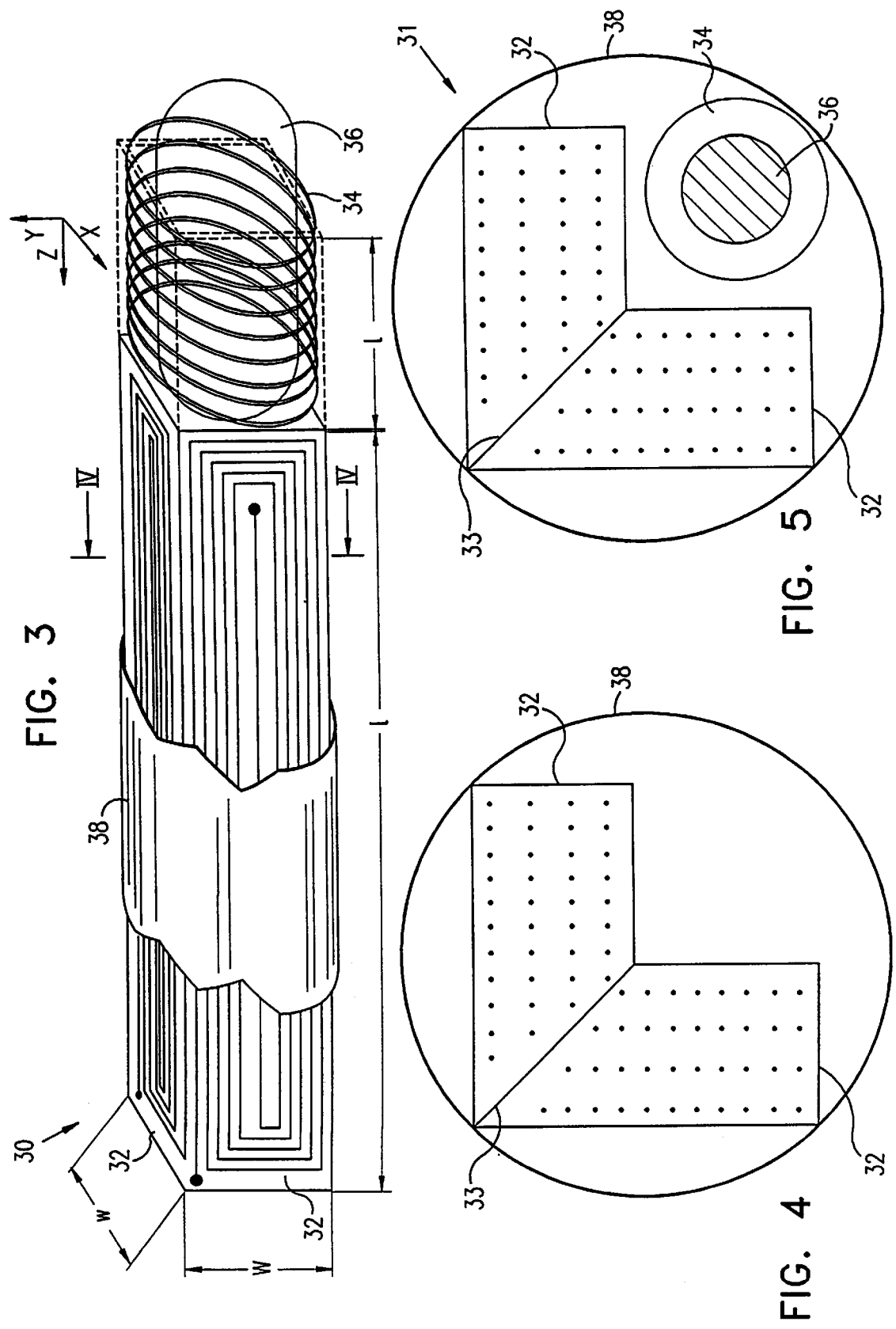

MINIATURIZED POSITION SENSOR HAVING PHOTOLITHOGRAPHIC COILS FOR TRACKING A MEDICAL PROBE

CROSS-REFERENCE TO RELATED APPLICATIONS

This application is a nonprovisional patent application of copending provisional patent application: U.S. Ser. No. 60/061,269 filing date Oct. 7, 1997.

FIELD OF THE INVENTION

The present invention relates generally to object tracking systems, and specifically to non-contact, electromagnetic methods and devices for tracking the position and orientation of a medical probe.

BACKGROUND OF THE INVENTION

In many medical procedures, probes, such as endoscopes and catheters, are inserted into a patient's body. Such probes are used for a large variety of procedures including irreversible surgical actions, such as ablation and taking of tissue samples. Therefore, it is necessary to have accurate information on the position and orientation of the probe within the patient's body.

Electromagnetic position determining systems provide a convenient method of receiving accurate information on the position and orientation of intra-body objects, and allow accurate tracking of these objects. Such systems are described for example in U.S. Pat. Nos. 5,558,091, 5,391,199 and 5,443,489, and in International Patent Publications WO94/04938 and WO96/05768, whose disclosures are incorporated herein by reference. These systems determine the coordinates of a probe using one or more field sensors, such as a Hall effect device, coils or other antennas carried on the probe. The transducers are typically located at or adjacent the distal end of the probe, and/or along the length of the probe. Therefore, the transducers are preferably made as small as possible so as to fit into the probe without interfering with the probe's maneuverability or increasing its size unduly.

U.S. Pat. No. 5,558,091 describes a Hall effect sensor assembly of a cube shape which includes three mutually orthogonal, thin galvanomagnetic films. This sensor assembly is preferably of dimensions about 3×0.75×0.75 mm. The 5,558,091 Patent further describes another Hall effect sensor assembly which includes three field sensing elements in the form of semiconductor chips. Each chip includes one or more elongated bars of a magnetoresistive material. Each such chip is sensitive to magnetic field components in the direction of the bar. This assembly preferably has a diameter of 0.8 mm or less. However, such chips suffer from nonlinearities, saturation effects, hysteresis and temperature drifts.

Therefore, most magnetic position determining systems use sensors formed of miniature coils that include a large number of turns of an electrically conducting wire. Such coils are described, for example, in PCT publications PCT/GB93/01736, WO94/04938 and WO96/05768, in the above mentioned U.S. Pat. No. 5,391,199, and in PCT publication PCT/IL97/00009, which is assigned to the assignee of the present application, all of which are incorporated herein by reference. The performance of a sensor coil is dependent on its inductance, which is a function of the number of turns of the coil times the cross sectional area of the coil. Therefore, in planning a miniature coil for use within a surgical probe, for example, it is generally necessary to make a compromise between performance and the size of the coil. Such coils typically have minimum dimensions of 0.6×0.6×0.6 mm and more generally of 0.8×0.8×0.8 mm. Smaller coils of the same type would not provide acceptable performance and are also hard to manufacture.

In order to determine both translational and rotational coordinates, some position determining systems, such as the system described in the above-mentioned PCT publication WO96/05768, use three sensor coils, having respective axes that are mutually linearly independent, preferably mutually orthogonal. Preferably, these three coils are packaged together to form a sensor assembly, which is used to provide six-dimensional position and orientation coordinate readings. The use of an assembly which has the three coils within one package allows easy insertion and/or attachment of the coils to catheters. Also, the assembly provides exact positioning of the coils relative to each other, thus simplifying the calibration of position determining systems using the coils. Generally, the coils are enclosed in a cylindrical-shaped case, which protects the coils from the surroundings.

In the system of the '768 publication, this assembly typically has a length of about 6 mm and a diameter of about 1.3 mm. Because the axes of the coils need to be generally mutually orthogonal in order to achieve accurate position sensing in all six dimensions, it is not possible to make the diameter of the assembly much smaller.

Although this coil assembly fits into most medical probes, in some cases coils of equivalent performance and smaller width are desired. For example, PCT patent application PCT/IL97/00061, which is assigned to the assignee of the present invention and is incorporated herein by reference, describes a method of enhancing the accuracy of position determination of an endoscope that includes miniature position sensing coils, by distancing the coils from metallic apparatus within the endoscope. If the coil assembly can be made with a smaller width, it is then possible to increase the separation between the miniature coils and the metallic apparatus, and thus achieve better accuracy from the position determining system.

Reducing the width of the coil assembly also allows position determining systems to be used with narrower probes, which generally have superior maneuverability and ease of access to remote locations. Alternatively, reducing the width of the coil assembly allows the assembly to occupy a smaller portion of the cross-sectional area of the probe, leaving more space for functional apparatus and/or working channels along the probe.

Coils made by photolithography or VLSI procedures are known in the art. In the following disclosure and in the claims, these coils are referred to as photolithographic coils. Photolithographic coils are generally made in the form of a spiral conductor printed on a substrate of plastic, ceramic or semiconductor material. Such coils conventionally comprise up to four overlapping spiral layers, using currently available fabrication techniques.

Photolithographic coils or antennas are also commonly used in contactless smart cards, as are known in the art. These cards inductively communicate with and receive power from a reader circuit through a photolithographic coil or antenna embedded in the card. Because smart cards are limited in thickness to less than 0.8 mm, they generally include only a single coil, whose axis is necessarily perpendicular to the plane of the card. To communicate with the reader, the smart card must be properly oriented, so that the coil axis is aligned with a magnetic field generated by the reader, in order to achieve proper coupling.

SUMMARY OF THE INVENTION

It is an object of some aspects of the present invention to provide a sensor coil with reduced thickness but high sensitivity and/or q-factor.

It is another object of some aspects of the present invention to provide a coil assembly including three orthogonal coils having a narrow, elongate shape.

In preferred embodiments of the present invention, a coil assembly comprises three coils of which at least one, and preferably two, comprise photolithographic coils. The coils have axes which are mutually linearly independent, preferably the axes are mutually substantially orthogonal. The use of these photolithographic coils allows forming coil assemblies with reduced diameter, width and/or depth, as described below.

In some of these preferred embodiments, two of the coils comprise long, narrow photolithographic coils. The length of the coils compensate for the narrow width, so that the coil encompasses a large enough area to give sufficient inductance for use as a position sensor in a position determining system. Preferably, the width of the coil is less than 0.8 mm, most preferably less than 0.6 mm. The thickness of the coils is preferably limited only by the photolithographic process and is generally about 0.3 mm. In a preferred embodiment of the present invention, the photolithographic coils are produced on a flexible substrate, so that the assembly does not restrict the flexibility of a catheter carrying the assembly.

In a preferred embodiment of the present invention, an assembly comprises two long, narrow photolithographic coils which are aligned with their long sides adjacent each other and substantially at 90° with respect to each other. Thus, the photolithographic coils define a long, narrow box shape, having a longitudinal axis to which the coil axes of the two photolithographic coils are substantially perpendicular.

Preferably, the substrates of the photolithographic coils are cut diagonally at an angle of about 45°, so that the substrates are adjacent each other at the diagonal cuts. This connection saves space and minimizes the volume required by the assembly.

The third coil, preferably a miniature wire-wound coil, is positioned with its coil axis along the longitudinal axis. Preferably, the third coil is outside and adjacent to the box shape, so that the width and depth of the assembly are substantially minimized. Alternatively, the diameter of the wire coil is smaller than the width of the photolithographic coils, and the wire coil is placed within the box shape defined by the photolithographic coils. Thus, the coil assembly has narrow width and depth, preferably smaller than 0.8 mm, most preferably about 0.6 mm, such that the diameter of a cylinder enclosing the assembly is no more than about 0.9 mm. Consequently, the cross-sectional area of the assembly is preferably less than 1 mm$^2$, more preferably less than 0.8 mm$^2$, and most preferably less than 0.65 mm$^2$.

Preferably, a long, ellipsoidal ferrite core is contained inside the angle formed by the two photolithographic coils. Preferably, the wire coil is also wound around a core, most preferably around the long ellipsoidal core. The ferrite core enhances the inductance of the assembly and therefore the sensitivity of the coil assembly. Preferably the assembly is enclosed within a cylinder shaped case which protects the coils from the surroundings.

In another preferred embodiment of the present invention, a plurality of small photolithographic coils are used to form the third coil. Preferably, the small coils are placed parallel each other, orthogonal to the first two coils, within the box shape defined by those coils, as described above. The small coils preferably have a rectangular shape with a width of about 0.4 mm, such that the small coils do not protrude from the box shape or from a cylinder encompassing the box shape. Alternatively, the plurality of photolithographic coils are placed outside the box shape of the first two coils but along the longitudinal axis thereof.

In some preferred embodiments of the present invention, the coil assembly may comprise three photolithographic coils, the axes of which are mutually linearly independent.

In some preferred embodiments of the present invention, one or more photolithographic coil assemblies, as described above, are placed within a medical probe to allow determination of coordinates of the probe, preferably six-dimensional position and orientation coordinates. In these assemblies, each coil preferably has a separate wire connection, so that the sensed effect of an external magnetic field on each coil is determined independently. A position determining system determines the position and orientation of the assembly based on the sensed effect on all three coils, as described, for example, in the above-mentioned WO96/05768 patent publication.

Use of assemblies with photolithographic coils allows substantial decrease of the diameter of the cylinder encompassing the coils. This decreased diameter allows easier attachment or embedding of the assembly in the probe. A smaller assembly also makes it possible to use smaller probes, and/or reduces interference of the assembly with working channels and functional apparatus in the probe. Also, small width and thickness of the coil allow larger separation between the coil and metallic apparatus in the probe, thus minimizing interference with the operation of the position determining system.

In other preferred embodiments of the present invention, a photolithographic coil assembly is used for inductive transfer of power and/or information. In these preferred embodiments, the three coils in the assembly are preferably connected together in series or in parallel. Such inductive information transfer is used, for example, in smart cards, as described above. The narrow width of the photolithographic coil assembly makes it especially suitable for use in smart cards, which generally must be no thicker than 0.8 mm. Using this coil assembly makes the coupling between the smart card and the reader substantially insensitive to the angle between the Smart Card and the reader, since the axes of the coil assembly are mutually linearly independent.

Similarly, such photolithographic coil assemblies may be used in intrabody tube location confirmation devices, as described, for example, in a PCT Patent Application filed Sep. 15, 1997, entitled "Position Confirmation with Learn and Test Functions," and filed as U.S. patent application Ser. No. 09/079,338 which is assigned to the assignee of the present invention and is incorporated herein by reference.

There is therefore provided, in accordance with miniature coil assembly for transmitting or receiving magnetic waves including a plurality of coils, each coil having a respective axis, assembled such that at least two of the axes are mutually linearly independent, and such that all of the plurality of coils are contained within a volume having a cross-sectional area substantially less than 1.0 mm$^2$, preferably substantially less than 0.8 mm$^2$, and most preferably substantially less than 0.65 mm$^2$.

Preferably, at least two of the coils include photolithographic coils.

There is further provided, in accordance with a preferred embodiment of the present invention, a miniature coil assembly for transmitting and receiving magnetic waves including two photolithographic coils having respective, mutually linearly independent axes.

Preferably, the photolithographic coils have a width smaller than 0.8 mm, and more preferably smaller than 0.65 mm.

Preferably, the axes of the two photolithographic coils are mutually substantially orthogonal.

In a preferred embodiment of the invention, the assembly includes a third coil, wherein the axis of the third coil and of the two photolithographic coils are mutually linearly independent. Preferably, the axis of the third coil is substantially orthogonal to the axes of the two photolithographic coils.

In one preferred embodiment, the third coil is a wire-wound coil, whereas in another preferred embodiment, the third coil includes a plurality of interconnected photolithographic circuits.

Preferably, the two photolithographic coils include elongate rectangular substrates having a long side and a narrow side, and the two photolithographic coils are aligned such that the long sides of the two coils are mutually adjacent. Preferably, the substrates of the two photolithographic coils are aligned substantially at a right angle with respect to one another.

Preferably, the assembly is circumscribed by a cylindrical volume having a diameter smaller than 1.1 mm, more preferably smaller than 0.9 mm.

In a preferred embodiment, the assembly includes a ferromagnetic core for enhancing the inductance of the coils, preferably an elongate ellipsoidal ferrite.

Preferably, the ferrite serves as a common core for substantially all of the coils in the assembly.

Preferably, a position determining system receives signals generated by the coils responsive to an electromagnetic field and analyzes the signals to determine coordinates of the coils. Preferably, the coils are inserted in an invasive medical probe, for finding coordinates of the probe, preferably six-dimensional position and orientation coordinates.

There is also provided, in accordance with a preferred embodiment of the present invention, a method for determining the position of an object including:

attaching a photolithographic coil assembly to the object; and receiving signals from the assembly to determine coordinates thereof.

Preferably, attaching the assembly includes embedding the photolithographic coils within the object.

Further preferably, attaching the coil assembly includes fixing two photolithographic coils having respective axes to the object such that the axes of the two coils are mutually linearly independent, and so as to define a volume having a cross-sectional area substantially less than 1 mm$^2$.

There is additionally provided, in accordance with a preferred embodiment of the present invention, a probe whose position is tracked within the body of a subject, including:

an insertion tube; and a photolithographic coil assembly attached to the insertion tube.

Preferably, the assembly is contained within a volume having a cross-sectional area substantially less than 1.0 mm$^2$.

Further preferably, the photolithographic coil assembly includes at least two photolithographic coils and, preferably, a wire-wound coil, wherein the coils preferably have respective axes that are mutually linearly independent and, most preferably, mutually substantially orthogonal.

In a preferred embodiment of the invention, a position determining system receives signals from the coils and analyzing the signals to determine coordinates of the probe.

The present invention will be more fully understood from the following detailed description of the preferred embodiments thereof, taken together with the drawings, in which:

BRIEF DESCRIPTION OF THE DRAWINGS

FIG. 1 is a schematic perspective view of a photolithographic coil, in accordance with a preferred embodiment of the present invention;

FIG. 2 is a schematic exploded view of the photolithographic coil of FIG. 1;

FIG. 3 is a schematic, isometric view of a coil assembly, in accordance with a preferred embodiment of the present invention;

FIG. 4 is a sectional view of the assembly of FIG. 3 taken along line IV—IV;

FIG. 5 is a schematic, sectional view of a coil assembly, in accordance with a preferred embodiment of the present invention;

DETAILED DESCRIPTION OF PREFERRED EMBODIMENTS

Figure 6:
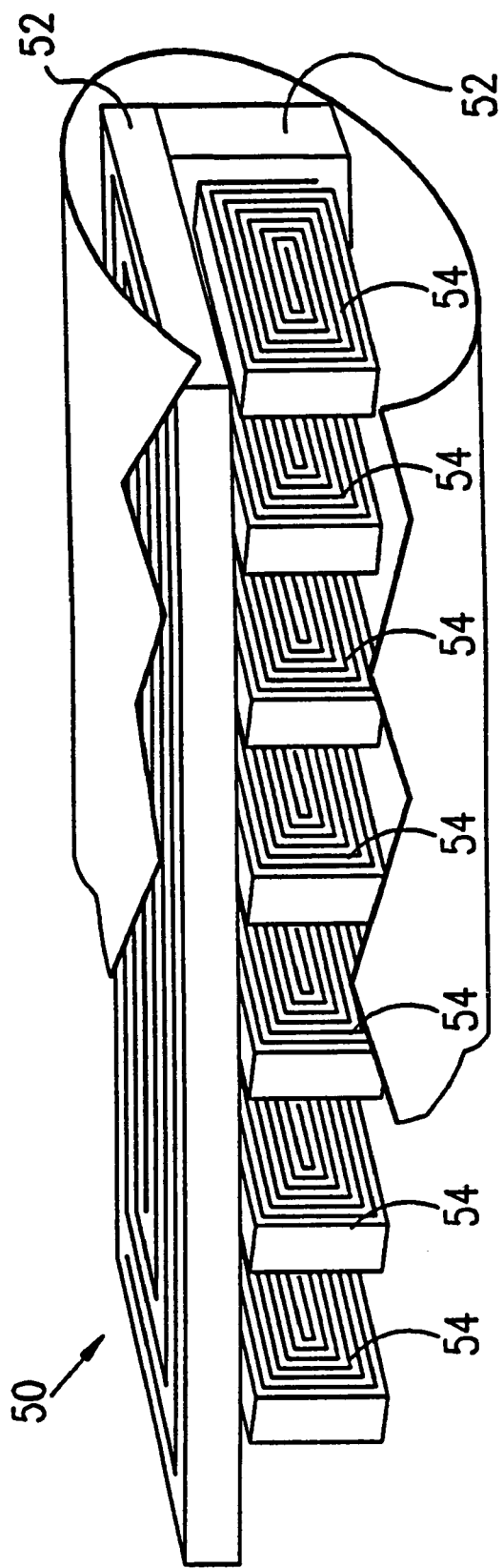
FIG. 6 is a schematic, isometric view of a coil assembly, in accordance with a preferred embodiment of the present invention.

FIGS. 1 and 2 show a sensor coil 10 made using a photolithographic method, in accordance with a preferred embodiment of the present invention. FIG. 1 shows a schematic view of coil 10, and FIG. 2 shows an exploded view of coil 10, which contains a plurality of layers 18, ordinarily four, the number of which is limited practically by the limitations of current photolithographic technology. Each layer 18 contains a conducting spiral 12, which is deposited on a substrate 14 of an electrically insulating material. External ports 16 positioned at the ends of spiral 12 allow electric access to coil 10, as is known in the art. Wires 26, which are connected to ports 16, couple coil 10 to a position determining system or alternatively to a transmitter (not shown in the figures), which provides wireless transmission of signals to the position determining system.

Substrate 14 preferably comprises a long, narrow, rectangular-shaped flat piece. Preferably, substrate 14 has a thickness of approximately 0.3 mm as is known in the art. The width (w) of substrate 14 is approximately between 0.4 and 0.7 mm, preferably 0.6 mm. Preferably, the length (L1) of substrate 14 is between about 4 and 5 mm.

Spiral 12 contains a plurality of loops 20 of diminishing size. Preferably, loops 20 are as large as possible, leaving only a minimal distance between each two adjacent loops, as required by VLSI technology rules, so as to encompass a maximal area. Spirals 12 of different layers are connected at vias 22, as is known in the art.

Coil 10 is suitable for use as a near field sensor, especially for sensing electromagnetic fields alternating at a frequency between 1–5 kHz.

FIG. 3 shows a coil assembly 30, in accordance with a preferred embodiment of the present invention. Assembly 30 comprises two photolithographic coils 32, such as coil 10 of FIG. 1, and a wire coil 34. Wire coil 34 preferably has a diameter of about 0.8 mm and a length (L2) of about 1.4 mm, in which there are preferably about 400 turns. Coils 32 are aligned with their long sides adjacent each other and at approximately 90° with respect to each other, substantially defining a box shape. Preferably, wire coil 34 is positioned in a longitudinal extension of the box shape, so as not to add to the width or depth of assembly 30.

Preferably, wire coil 34 is wound around a ferrite core 36, which enhances the inductance of the coil. More preferably, ferrite core 36 is long and narrow and is contained both within wire coil 34 and within the box shape defined by coils 32. Thus, ferrite core 36 enhances the inductance of all of the coils in assembly 30.

Preferably, assembly 30 is enclosed within a cylindrical case 38, which has a diameter approximately equal to or slightly greater than a diagonal of the box shape defined by photolithographic coils 32.

FIG. 4 shows a cross-section of the assembly of FIG. 3 taken along line IV—IV. Preferably, along a common edge 33 between coils 32, the substrates of the coils are cut diagonally to reduce the volume taken up by coil assembly 30. Alternatively, the substrates may be cut square, and one of coils 32 may be made wider than the other.

FIG. 5 shows a coil assembly 31, in accordance with an alternative embodiment of the present invention. Assembly 31 is similar to assembly 30, except that in assembly 31, wire coil 34 is contained within the box shape defined by photolithographic coils 32, and possibly extends therefrom into case 38. Wire coil 34 has a diameter smaller than the width (w) of coils 32, preferably approximately 0.4 mm. In this embodiment, wire coil 34 preferably has between about 600 and 800 turns, in order to compensate for its small diameter.

It will be observed that assembly 30 includes three substantially orthogonal coils, i.e., the axes of the coils are mutually substantially orthogonal. Therefore, assembly 30 may conveniently be used in apparatus such as a position determining system with six degrees of freedom. The size of assembly 30 is limited by coils 32, wherein its diameter is determined by the width (w) of coils 32, and the length of assembly 30 is substantially the length (L1) of coils 32.

In a preferred embodiment of the present invention, not shown in the figures, a coil assembly such as assembly 30 is embedded within a contactless smart card, for receiving power from and transferring information to a card reader. The coils of the assembly are preferably connected in series so that a magnetic field incident on the card induces a substantial current in the assembly, regardless of the orientation of the card relative to the field. Alternatively, the coils may be connected to each other in parallel. Due to the small dimensions of the assembly of the present invention, it is possible to insert it into conventional smart cards, which are typically limited in thickness to no more than about 0.8 mm.

FIG. 6 shows a coil assembly 50, in accordance with an alternative embodiment of the present invention. Assembly 50 comprises two photolithographic coils 52 similar to coil 10 of FIG. 1. Preferably, coils 52 are aligned relative to each other in a manner similar to assembly 30. A plurality of small coils 54 are situated within a box shape defined by coils 52. Coils 54 are preferably similar to coils 52 although of smaller width and length, so that they fit in the box shape. Coils 54 are preferably connected in series. Thus, the small size of coils 54 is compensated for by the use of a number of coils. Preferably, coils 54 are aligned such that they have a common axis, which is perpendicular to the axes of coils 52, forming together with coils 52 an assembly of three perpendicular sensors.

Figure 7:
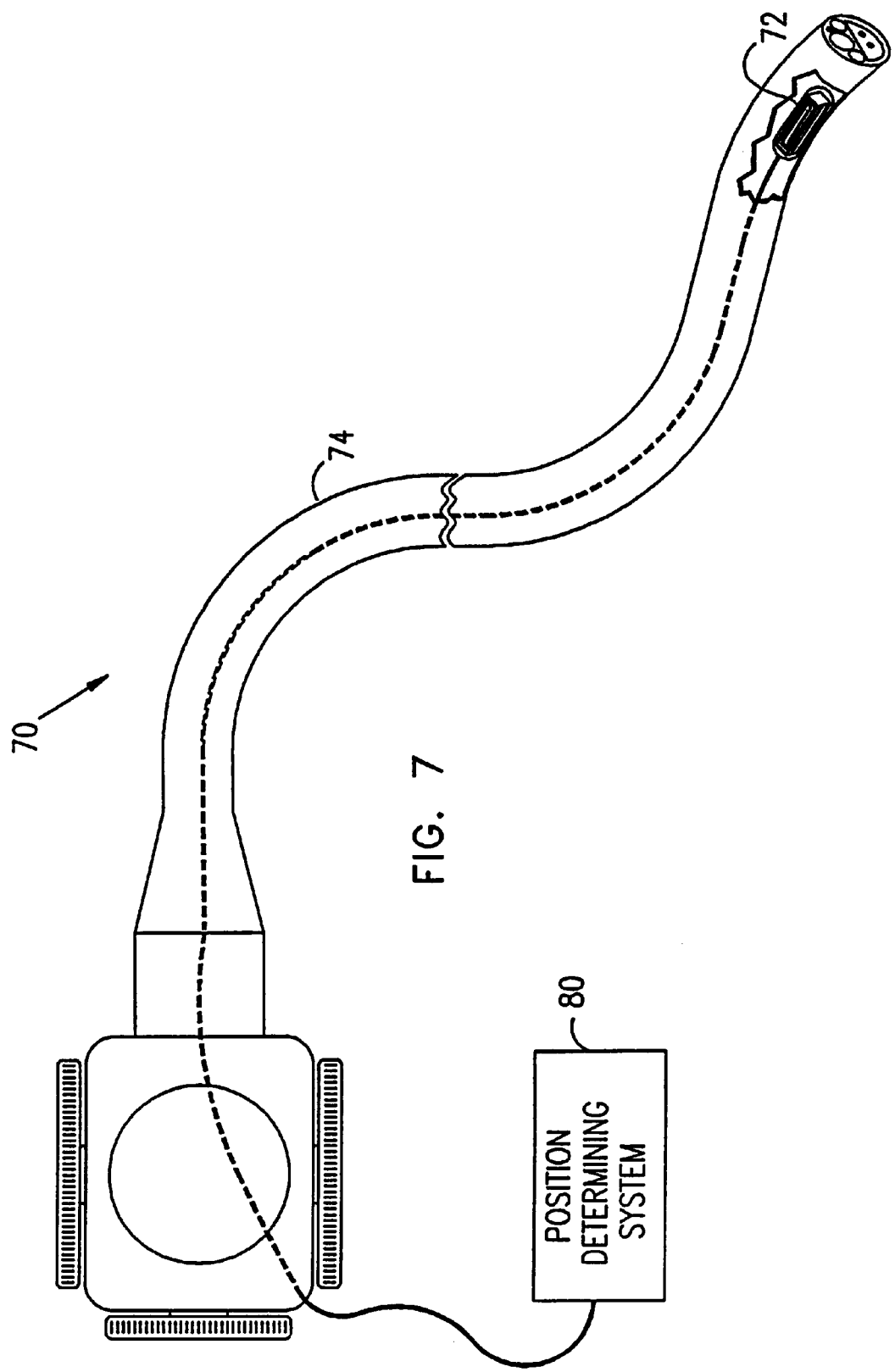
FIG. 7 is a schematic illustration of a catheter including a coil assembly, in accordance with a preferred embodiment of the present invention.

FIG. 7 shows a catheter 70 including a photolithographic coil assembly 72, in accordance with a preferred embodiment of the present invention. Catheter 70 comprises an insertion tube 74, which is inserted into a patient's body. Coil assembly 72 is preferably a miniature assembly, similar to assembly 30 or 31, as described above, and is preferably situated adjacent the distal end of insertion tube 74. As described, for example, in the above-mentioned PCT publication WO96/05768, the coils in assembly 72 generate signals responsive to an external magnetic field applied thereto. A position determining system 80 coupled to coil assembly 72 receives the signals and accordingly determines position and orientation coordinates of the coil assembly and hence, the position and orientation of the catheter.

The insertion tube of a catheter normally has a diameter of about 1–5 mm. A catheter having a round insertion tube of 3 mm diameter has a cross section of about 7 mm$^2$. Assembly 72 has a cross section of about 0.6 mm$^2$, thus taking up less than 10% of the cross sectional area of the catheter. Hence, assembly 72 does not substantially interfere with the operation of the catheter.

Preferably, assembly 72 is distanced from metallic and other substances in catheter 70 which may interfere with magnetic position determination, as described in the above-mentioned PCT/IL97/00061 patent application. The small width of assembly 72 allows larger separation from such interfering substances than other sensor assemblies. Endoscopes frequently comprise insertion tubes that include metallic substances. These insertion tubes normally have a diameter of about 12–15 mm. If the insertion tube has a metal core with a diameter of about 8 mm, it is possible to have over 2.5 mm separation between the metal core and coil assembly 72. Such separation is sufficient to reduce substantially interference caused by the metal core in position determination of the tube.

It is noted that insertion of assembly 72 into a catheter is simple and does not require any special design characteristics of the catheter. Thus, assembly 72 may be inserted into existing catheters with relatively minimal change to the catheter's design.

It will be appreciated that the preferred embodiments described above are cited by way of example, and the full scope of the invention is limited only by the claims.

What is claimed is:

1. A miniature coil assembly for transmitting or receiving magnetic waves for tracking a medical probe, the assembly comprising a plurality of coils, each coil having a respective axis, assembled such that at least two of the axes are mutually linearly independent, and such that all of the plurality of coils are contained within a volume having a cross-sectional area less than 1.0 mm$^2$, wherein at least two of the coils comprise photolithographic coils having respective, mutually linearly independent axes, the axes of the two photolithographic coils being mutually substantially orthogonal, and a third coil, wherein the axis of the third coil and of the two photolithographic coils are mutually linearly independent, the axis of the third coil being substantially orthogonal to the axes of the two photolithographic coils.

2. The coil assembly of claim 1, wherein all of the plurality of coils are contained within a volume having a cross-sectional area less than 0.8 mm$^2$.

3. The coil assembly of claim 2, wherein all of the plurality of coils are contained within a volume having a cross-sectional area less than 0.65 mm$^2$.

4. The coil assembly of claim 1, wherein the photolithographic coils have a width smaller than 0.8 mm.

5. The coil assembly of claim 1, wherein the photolithographic coils have a width smaller than 0.65 mm.

6. The coil assembly of claim 1, wherein the third coil is a wire-wound coil.

7. The coil assembly of claim 1, wherein the third coil comprises a plurality of interconnected photolithographic circuits.

8. The coil assembly of claim 1, wherein the two photolithographic coils comprise elongate rectangular substrates having a long side and a narrow side, and the two photolithographic coils are aligned such that the long sides of the two coils are mutually adjacent.

9. The coil assembly of claim 8, wherein the substrates of the two photolithographic coils are aligned substantially at a right angle with respect to one another.

10. The coil assembly of claim 9, wherein the assembly is circumscribed by a cylindrical volume having a diameter smaller than 1.1 mm.

11. The coil assembly of claim 10, wherein the cylindrical volume has a diameter smaller than 0.9 mm.

12. The coil assembly of claim 10, and comprising a ferromagnetic core in said volume for enhancing the inductance of the coils.

13. The coil assembly of claim 12, wherein the core comprises an elongate ellipsoidal ferrite.

14. The coil assembly of claim 13, wherein the ferrite serves as a common core for substantially all of the coils in the assembly.

15. The coil assembly of claim 1, including a position determining system for receiving signals generated by the coils responsive to an electromagnetic field and analyzing the signals to determine coordinates of the coils.

16. The coil assembly of claim 15, wherein the coils are inserted in an invasive medical probe, for finding coordinates of the probe.

17. The coil assembly of claim 16, wherein the coordinates comprise six-dimensional position and orientation coordinates.

* * * * *